United States Patent
Sun et al.

(10) Patent No.: US 7,717,112 B2
(45) Date of Patent: May 18, 2010

(54) POSITIVE AIRWAY PRESSURE THERAPY MANAGEMENT MODULE

(75) Inventors: Jianguo Sun, 1175 Park Pl., #308, San Mateo, CA (US) 94403; Laughton E. Miles, Los Altos Hills, CA (US)

(73) Assignee: Jianguo Sun, Palo Alto, CA (US)

( * ) Notice: Subject to any disclaimer, the term of this patent is extended or adjusted under 35 U.S.C. 154(b) by 211 days.

(21) Appl. No.: 11/017,566

(22) Filed: Dec. 20, 2004

(65) Prior Publication Data

US 2005/0188991 A1   Sep. 1, 2005

Related U.S. Application Data

(63) Continuation-in-part of application No. 10/861,089, filed on Jun. 4, 2004, now abandoned.

(60) Provisional application No. 60/531,512, filed on Dec. 19, 2003, provisional application No. 60/476,213, filed on Jun. 4, 2003.

(51) Int. Cl.
  *A61M 16/00* (2006.01)
  *A61M 15/00* (2006.01)

(52) U.S. Cl. ............... 128/204.23; 128/200.24; 128/204.18; 128/204.21

(58) Field of Classification Search ........... 128/204.18, 128/204.21, 204.22, 204.26, 200.24, 204.23, 128/205.11, 5.25, 206.12, 206.21, 207.11
See application file for complete search history.

(56) References Cited

U.S. PATENT DOCUMENTS

| | | | | |
|---|---|---|---|---|
| 5,535,738 | A * | 7/1996 | Estes et al. | 128/204.23 |
| 5,590,648 | A * | 1/1997 | Mitchell et al. | 600/301 |
| 5,954,050 | A * | 9/1999 | Christopher | 128/204.21 |
| 6,158,433 | A * | 12/2000 | Ong et al. | 128/204.21 |
| 6,186,142 | B1 * | 2/2001 | Schmidt et al. | 128/204.23 |
| 6,349,724 | B1 * | 2/2002 | Burton et al. | 128/204.18 |
| 7,025,730 | B2 * | 4/2006 | Cho et al. | 600/529 |
| 7,204,250 | B1 * | 4/2007 | Burton | 128/205.23 |
| 2003/0015200 | A1 | 1/2003 | Hansen | |
| 2004/0019464 | A1 * | 1/2004 | Martucci et al. | 702/189 |
| 2004/0144383 | A1 * | 7/2004 | Thomas et al. | 128/204.18 |

(Continued)

OTHER PUBLICATIONS

PCTUS0661224, International Search Report & Written Opinion, Oct. 3, 2007.

*Primary Examiner*—Steven O Douglas
*Assistant Examiner*—Annette F Dixon
(74) *Attorney, Agent, or Firm*—Lathrop & Gage LLP (57) ABSTRACT

A positive airway pressure therapy management module includes a user interface, a controller and memory. The module may include ports that capture data from a PAP device and/or from sensors. The user interface may display information and questions, and may receive answers. The controller may store data while offline from the network, and may respond to requests over the network while online with the network. A software product includes instructions that, under control of a computer, perform steps for managing positive airway pressure therapy of a patient. A method for managing positive airway pressure therapy of a patient captures data and communicates the data over a network. The method may capture data from a PAP device and/or from sensors, display questions and receiving answers, and calculate indices and/or metrics, perform a pressure titration, and/or relay commands to a PAP device in response to commands from the network.

31 Claims, 7 Drawing Sheets

U.S. PATENT DOCUMENTS

| | | | |
|---|---|---|---|
| 2005/0115561 A1* | 6/2005 | Stahmann et al. | 128/200.24 |
| 2005/0121033 A1 | 6/2005 | Starr et al. | |
| 2005/0247315 A1 | 11/2005 | Estes et al. | |
| 2005/0268912 A1* | 12/2005 | Norman et al. | 128/204.23 |
| 2007/0044805 A1* | 3/2007 | Wedler et al. | 128/207.14 |

* cited by examiner

POSITIVE AIRWAY PRESSURE THERAPY MANAGEMENT MODULE

CROSS-REFERENCE TO RELATED APPLICATIONS

This application claims the benefit of priority to U.S. Provisional Patent Application No. 60/531,512, filed 19 Dec. 2003. This application is also a continuation-in-part of U.S. patent application Ser. No. 10/861,089, filed 4 Jun. 2004 now abandoned, which claims the benefit of priority to U.S. Provisional Patent Application No. 60/476,213, filed 4 Jun. 2003. Each of the above-mentioned applications is incorporated herein by reference.

BACKGROUND

Routine treatment of sleep disorders such as Obstructive Sleep Apnea ("OSA"), hypopnea, and others is often provided in home settings by the use of Positive Airway Pressure ("PAP") devices. OSA typically results from relaxation of a patient's muscles during sleep, causing partial or complete obstruction of the patient's airway. Snoring is associated with partial obstruction. Cessation of breathing, or apnea, is associated with complete obstruction, and may lead to choking, partial or complete awakening, or worse medical complications, such as cardiovascular disease. A related sleep occurrence called hypopnea is an incident of shallow breathing, which is often inconsequential but can have significant medical impact if prolonged. PAP devices include a mask placed over a patient's nose and/or mouth, through which air blows into the patient's airway while the patient sleeps. The air pressurizes the patient's airway to prevent or mitigate apnea and hypopnea, reducing medical risks and improving the patient's quality of sleep.

The therapeutic conditions (e.g., pressure) to be supplied by a PAP device are usually determined in a sleep lab. Sleep labs are usually characterized by extensive equipment in a fixed location used only at night. Sleep lab costs are generally high, since sleep lab equipment is not typically used during regular business hours, and since technical personnel are paid higher wages to work through the night. Scheduling sleep lab sessions entails matching the availability of the sleep lab facility and personnel to the availability of a patient for an overnight stay. These cost and scheduling issues generally work to restrict the practical time for sleep lab studies for a given patient to one night. The same issues work to discourage sleep lab sessions for follow-up care or post treatment evaluation. The sleep lab bed, surroundings, and equipment also constitute an unfamiliar sleep environment for the patient, which, unfortunately, can result in a disturbance to the very sleep patterns being evaluated. Studies show that 2-4 weeks of data may be required to determine the optimal therapeutic pressure for a patient.

The therapeutic conditions supplied by a PAP device and developed in the sleep lab are then fixed for future use of the PAP device in the patient's home. These therapeutic conditions may not be ideal for the patient, in that the patient's sleep patterns may be different at home than in the sleep lab setting. The therapeutic conditions best suited for the patient may also be affected from time to time by variables in the patient's life that were not present during a sleep lab session, e.g.: (a) prior consumption of a heavy meal, alcohol, and/or certain medications, (b) variations in patient's emotional state, stress level, sleep phase and/or total sleep time, and (c) the presence of upper airway allergies and/or infections.

SUMMARY

In one embodiment, a positive airway pressure therapy management module ("PTM module") includes: a user interface that captures prompted data; a controller that processes the prompted data and that communicates the prompted data over a network (e.g., the Internet); and memory that stores the prompted data. The PTM module may include a data port that captures PAP device data from a PAP device. The controller processes the PAP device data and communicates the PAP device data over the network. The user interface may display information and questions, and may receive answers as prompted data. The controller may store data in memory while offline from the network; and, when online with the network, it may respond to a request over the network to communicate stored data over the network. The PTM module may also include one or more ports that interface with sensors that provide sensor data of a patient. The controller may be configured to (1) calculate indices such as an Apnea Hypopnea Index or a Respiratory Disturbance Index, (2) perform a pressure titration using the PAP device, and/or (3) apply expert system analysis to diagnose occurrence of mask leaks and/or partial upper airway obstruction.

In another embodiment, a software product includes instructions for managing positive airway pressure therapy of a patient, including instructions for: (1) capturing PAP device data from a PAP device, (2) operating a user interface to present information and to capture responses as prompted data; (3) storing data in memory and retrieving data from memory; and (4) communicating data over a network. In further embodiments, the software product has instructions for capturing sensor data from one or more sensors and/or instructions for calculating an Apnea Hypopnea Index, a Respiratory Disturbance Index, an airleak metric, a partial upper airway obstruction metric, a patient compliance metric, and/or a pressure titration.

In another embodiment, a method manages positive airway pressure therapy of a patient by capturing data through a user interface as prompted data, and then communicating the prompted data as positive airway pressure data over a network (e.g., the Internet). The method may also (1) capture data from a PAP device and communicate the PAP device data over the network, (2) display questions and receiving answers, (3) capture sensor data from one or more sensors connected to the patient, (4) calculate an index that such as an Apnea Hypopnea Index and/or a Respiratory Disturbance Index in response to a command from the network, (5) perform a pressure titration in response to a command from the network, and/or (6) relay commands to a PAP device in response to commands from the network.

In another embodiment, a mask includes an SpO2 sensor. The mask may be usable with a positive airway pressure device. The mask may include a pneumatic subsystem that regulates pressure of the SpO2 sensor against a forehead of a patient. The pneumatic subsystem may include a bladder that presses the SpO2 sensor against the forehead. Pressure to the bladder may be supplied by a bellows connected with the bladder, and may be regulated by a controller that (a) senses the pressure with a forehead pressure sensor and (b) controls an actuator to manipulate the bellows, to change the pressure. The pressure may be regulated within a range of 40 mm to 60 mm of mercury. As an alternative to the pneumatic subsystem, the mask may include a mechanical subsystem that regulates pressure of the SpO2 sensor against the forehead of the patient.

DETAILED DESCRIPTION OF DRAWINGS

Figure 1:
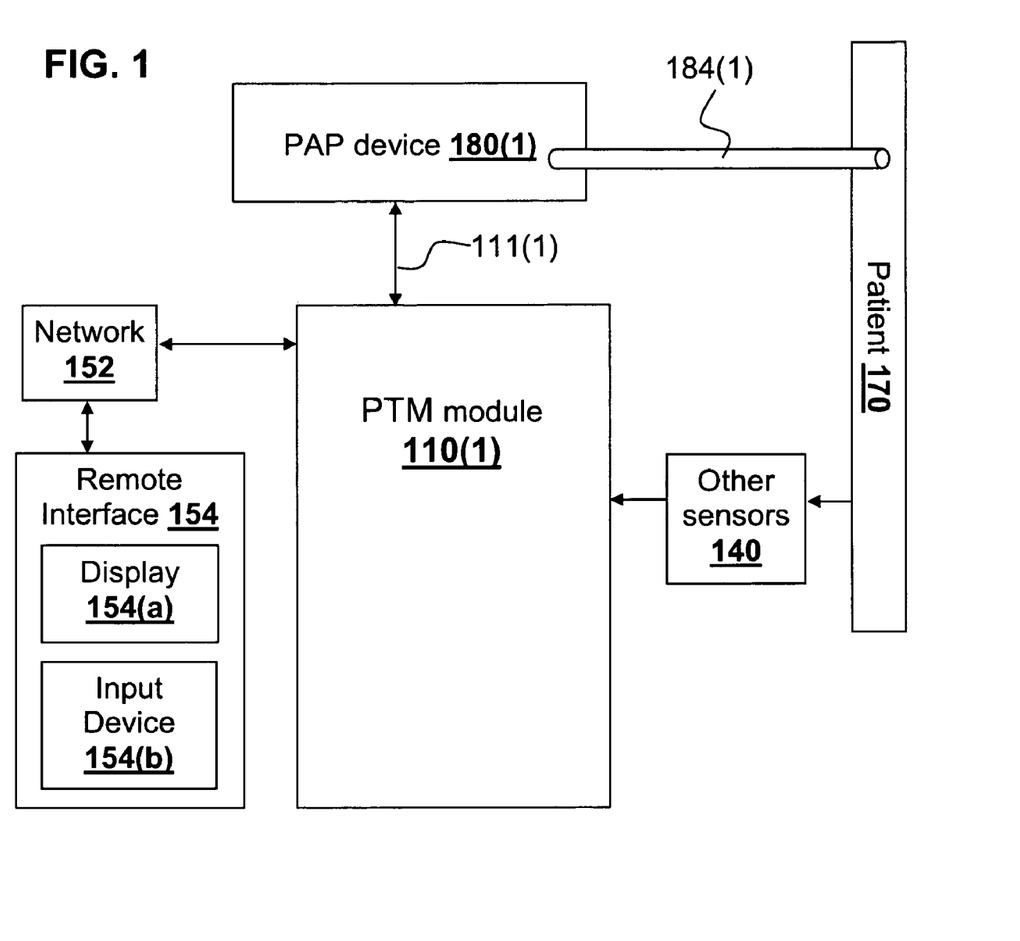
FIG. 1 shows one positive airway pressure therapy management (PTM) module embodiment in an operational setting.

FIG. 1 illustrates one Positive Airway Pressure Therapy Management (PTM) module 110(1), in operational use through connection with a PAP device 180(1) and sensors 140. Positive Airway Pressure (PAP) therapy is provided by PAP device 180(1) through an air hose 184(1) connected with an airway of a patient 170. PAP device 180(1) is for example a Continuous Positive Airway Pressure ("CPAP") device or a Bi-level Positive Airway Pressure device. PTM module 110(1) includes one or more electronic communication ports (described below) for sending or receiving data over a network 152, and for interfacing with external sensors 140.

In one embodiment, PAP device 180(1) has a communication port capable of providing data about its operation, for example data indicating use by patient 170, current therapeutic settings, and data regarding air pressure and flow delivered to patient 170. In this embodiment, PTM module 110(1) may communicate directly with PAP device 180(1), such as shown by data line 111(1).

As shown in FIG. 1, PTM module 110(1) may receive data from sensors 140 connected to patient 170. Sensors 140 for example provide data that augments data collected from PAP device 180(1). Exemplary sensors 140 may include, for example, air pressure and flow sensors, pulse oximetry ("SpO2") sensors, respiration effort sensors, snore sensors, and/or electrocardiogram ("EKG") sensors. PTM module 110(1) may operate independently from sensors 140.

In one embodiment, PTM module 110(1) communicates with a network 152, for example via telephone lines, modems, and other types of communication media. Network 152 is for example the Internet such that data of PTM module 110(1) may be uploaded, over network 152, to a server or Web site. Network 152 may also be a local area network of a sleep lab or hospital.

Connection between PTM module 110(1) and network 152 may provide for remote access and/or control of PTM module 110(1) and/or PAP device 180(1) by sleep technologists or medical professionals ("remote professionals") who may require or desire access thereto. For example, remote professionals can access information regarding (a) the number of nights the PAP device is used ("compliance"), and (b) the number of hours the PAP device has effectively treated the patient during the night ("efficacy"). Access to such information may enable intervention by remote professionals to improve compliance and efficacy. A remote interface 154 (e.g., a computer) may for example include a display 154(a) and an input device 154(b). Remote interface 154 is thus operable by remote professionals to display data communicated from, and issue commands to, PTM module 110(1), for example to provide feedback to patient 170, to calculate indices or metrics, and/or to modify the therapeutic conditions supplied by PAP device 180(1) to improve compliance and efficacy.

More particularly, if network 152 is the Internet, an on-line connection may be established before or during use by patient 170 of a PAP device 180(1), data gathered during the patient's use of PAP device 180(1) may also be uploaded to the Web site for real time use by remote professionals.

Real time access by remote professionals to data from PTM module 110(1) across a network 152 connection, and the issuance of remote commands to PTM module 110(1) (collectively, "remote supervision") may have certain advantages. For instance, remote supervision enables remote professionals to (1) monitor data from the patient 170, (2) issue a command to PTM module 110(1), and/or (3) monitor response to the command by PTM module 110(1), PAP device 180(1) and/or patient 170. One example of remote supervision is where a remote professional reviews data from patient 170 and commands PTM module 110(1) to direct PAP device 180(1) to raise or lower air pressure delivered to patient 170; the remote professional then monitors the response of patient 170. Another example of remote supervision is where a remote professional commands PTM module 110(1) to perform a pressure titration, and then monitors the response of patient 170 to the titration as it proceeds.

PTM module 110(1) may also gather and store data from patient 170 without connection to network 152. A connection between PTM module 110(1) and network 152 may be established later, at which time the data previously stored in PTM module 110(1) is, for example, communicated to network 152 as a single batch of data.

In one embodiment, PTM module 110(1) is used as an OSA diagnostic device. In one example, PTM module 110(1) receives data from sensors 140 attached to patient 170 (i.e., without PAP device 180(1)), and the data is processed and uploaded to network 152 for access by remote professionals. In many cases, the data allows remote professionals to definitively diagnose OSA (or the absence thereof), avoiding the use of a sleep lab to obtain the same result.

Figure 2:
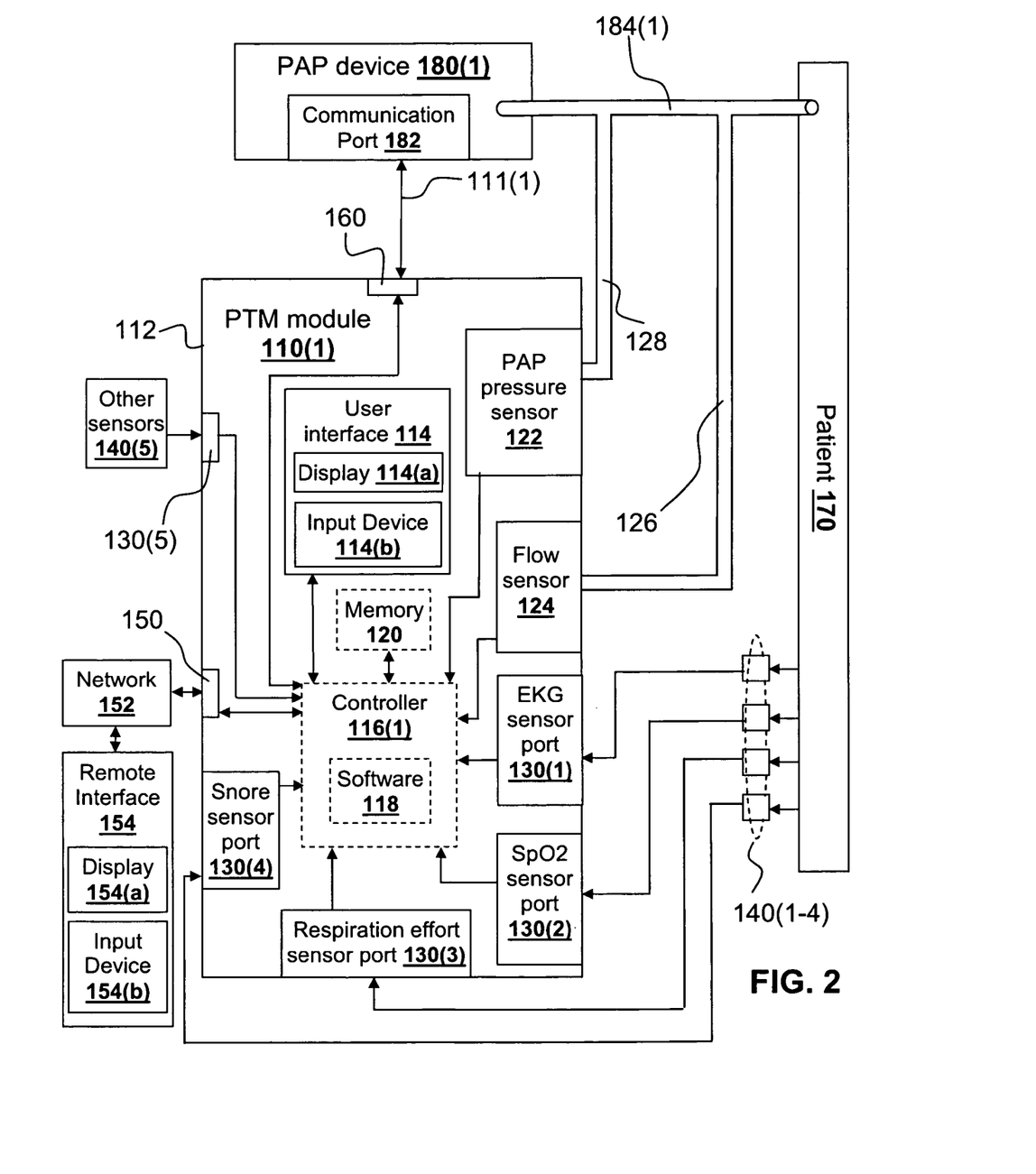
FIG. 2 illustrates exemplary detail of the positive airway pressure therapy management module of FIG. 1.

FIG. 2 illustrates exemplary detail of the positive airway pressure therapy management module of FIG. 1, in accord with one embodiment. In FIG. 2, PTM module 110(1) has a user interface 114, a controller 116(1), firmware 118, a memory 120 and a housing 112. User interface 114 may for example include a display 114(a) and an input device 114(b) (e.g., a keyboard); it is thus operable to display questions and to receive prompted data as answers. These questions and answers typically concern the patient's interaction with PAP device 180(1), or subjective perceptions of the patient about his or her quality of sleep or quality of life. User interface 114 may also be operable to provide information or suggestions to patient 170 without requiring a response.

Controller 116(1) is operable to process data of PTM module 110(1). This processing may include (1) storing and retrieving data from memory 120, (2) receiving and processing data from sensors 140 (and/or other sensors, e.g., sensors 122 and 124, described below), PAP device 180(1) and/or user interface 114, (3) performing calculations, and/or (4) sending data to and receiving data from network 152.

Firmware 118 is for example a set of instructions executable by controller 116(1) that enable PTM module 110(1) to carry out functions disclosed herein. Non-limiting examples of functions that may be performed by controller 116(1) in accordance with these instructions are (1) capture data from PAP device 180(1), sensors 140, and user interface 114, (2) store data in memory 120, (3) retrieve data from memory 120, (4) communicate data over network 152, (5) present data or other stored information to patient 170 through user interface 114, (6) calculate an Apnea Hypopnea Index or a Respiratory Disturbance Index, (7) perform a pressure titration, (8) analyze airway pressure variation to identify occurrences of snoring, (9) analyze airway flow and/or pressure data to identify the occurrence of mask leaks, e.g., the escape of air pressure provided by a PAP device 180(1) through a leak between a PAP device mask and a patient's face, (10) calculate a partial upper airway obstruction metric, (11) calculate a patient compliance metric, and/or (12) update or replace firmware 118, for example to update firmware over network 152.

Memory 120 of PTM module 110(1) may be a form of computer-readable memory media, such as volatile or non-volatile semiconductor or magnetic memory. Memory 120 may include fixed or removable media (e.g., floppy disks, semiconductor memory sticks), or a combination thereof. Memory 120 may be used for short term storage of data and results of calculations, or for storing up to several months of data and results of calculations for future upload over network 152, for example when PTM module 110(1) operates in an "off-line" mode (i.e., disconnected from network 152). Memory 120 may also be used to store information for presentation to patient 170, e.g., instructions to the patient regarding the use of PTM module 110(1), PAP device 180(1), and/or sensors 140.

PTM module 110(1) may further include a pressure sensor 122 connected to a tube 128 that connects with air hose 184(1). Sensor 122 samples the pressure in air hose 184(1) via tube 128 and provides data indicating the pressure to controller 116(1). PTM module 110(1) may further include a flow sensor 124 connected to a tube 126 that also connects with air hose 184(1); the connection of flow sensor 124 with air hose 184(1) is typically through a mask (not shown) through which pressurized air is suppliet to the patient through air hose 184(1). Sensor 124 samples the pressure in tube 126 and provides data, indicating air flow to the patient, to controller 116(1).

In one embodiment, PTM module 110(1) further includes one or more electronic ports, for example electronic ports 130(1)-130(5) that connect to sensors 140(1)-140(5), as shown. In such a configuration, sensors 140 may operate to measure physical attributes of a patient 170 and to provide associated data that is communicated, through ports 130, to controller 116(1). In an illustrative embodiment, sensor 140 (1) is a flow sensor; sensor 140(2) is an EKG sensor; sensor 140(3) is an SpO2 sensor; sensor 140(4) is a respiration effort sensor; and sensor 140(5) is a snore sensor. PTM module 110(1) may include other ports 130(5) for interfacing with other sensors 140(5), if desired.

A port 160 may be used to interface to a PAP device 180(1) which has a similar port 182 to facilitate communication between PAP device 180(1) and PTM module 110.

Figure 3:
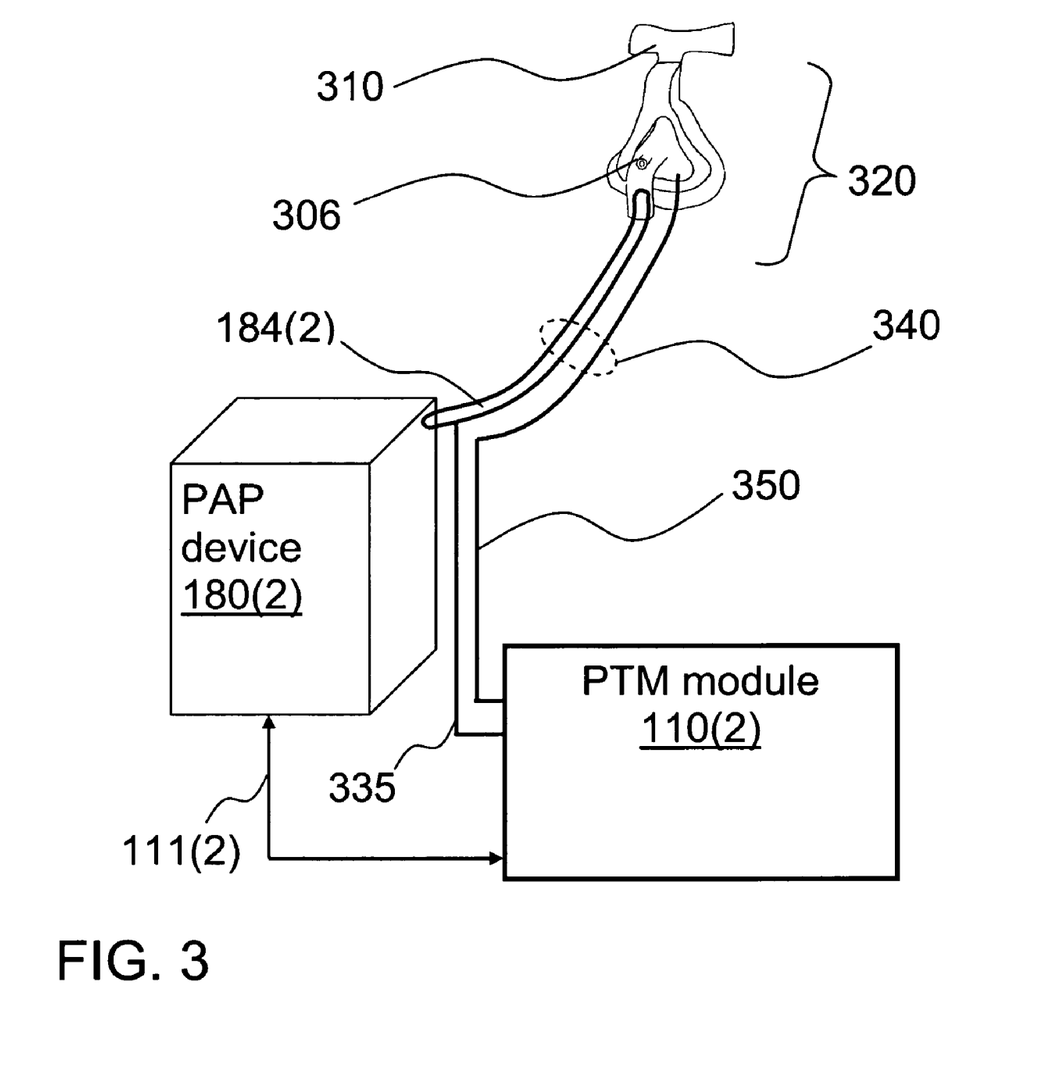
FIG. 3 shows exemplary relationships and connections among a PAP mask, a PAP device and a PTM module.

FIG. 3 shows exemplary relationships and connections among a PAP mask 320, a PAP device 180(2) and a PTM module 110(2), in accord with one embodiment. PAP mask 320 has a nasal element 306 and a forehead support 310; in use, a patient (not shown) straps nasal element 306 over his or her nose, and straps forehead support 310 to his or her forehead to stabilize PAP mask 320 while sleeping. A PAP air hose 184(2) connects nasal element 306 with air supplied by PAP device 180(2). A sensor harness 350 may include wires and/or tubes (see FIG. 4 and FIG. 5) that connect elements of PAP mask 320 with PTM module 110(2). Sensor harness 350 and air hose 184(2) may be coupled together (e.g., by strapping) to form an air tube harness 340, to avoid inconveniences caused by loose wires and tubes. A PAP pressure monitoring tube 335 connects with air hose 184(2) in the vicinity of PAP device 180(2), and connects with PTM module 110(2). PAP device 180(2) and PTM module 110(2) connect via data line 111(2).

Figure 4:
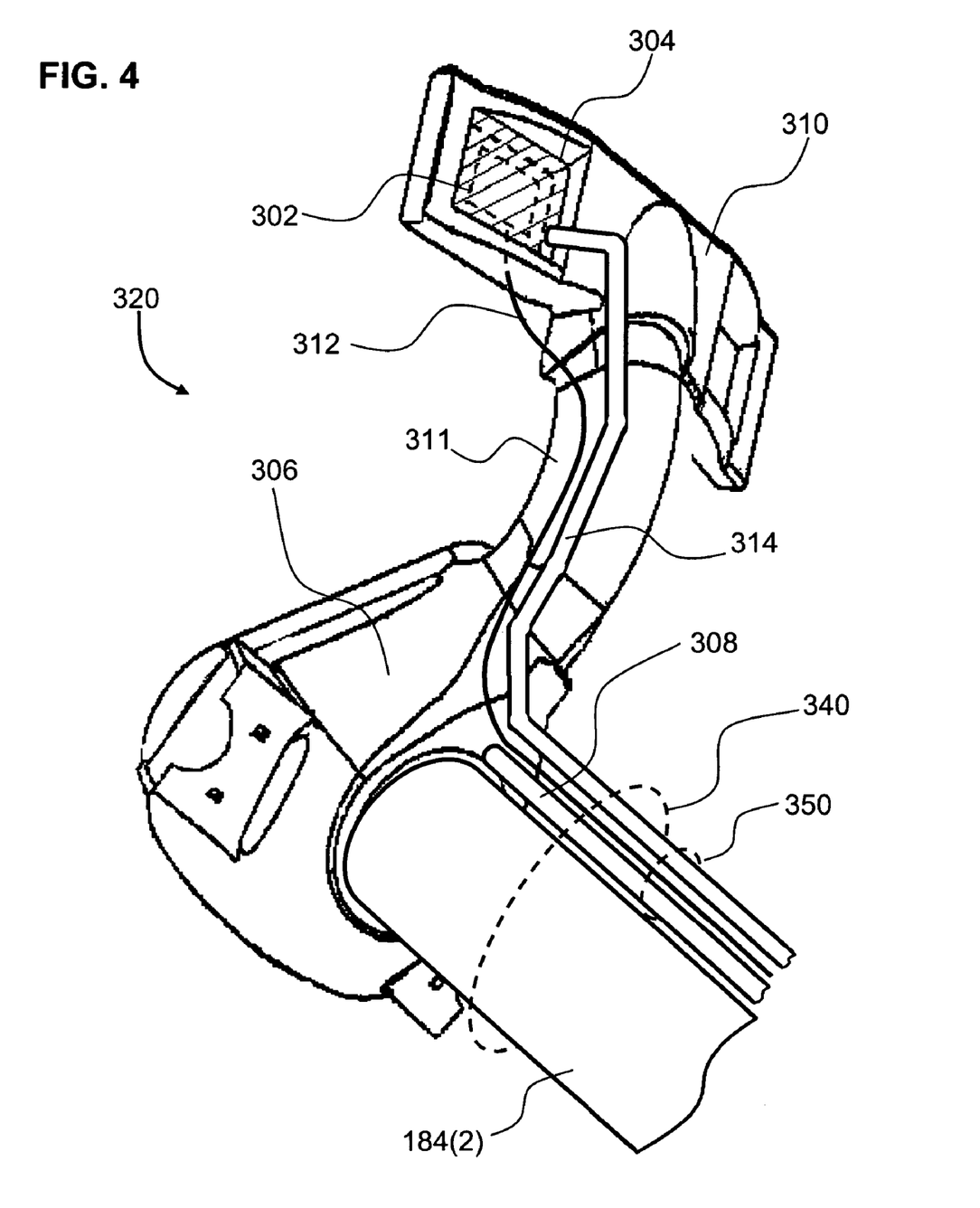
FIG. 4 shows exemplary detail of the PAP mask of FIG. 3.

FIG. 4 shows exemplary detail of PAP mask 320, in accord with one embodiment. Nasal element 306 connects with PAP air hose 184(2), and connects with a smaller tube 308 that connects with a flow sensor port in a PTM module (e.g., PTM module 110). Nasal element 306 structurally couples with forehead support 310, such as through structural member 311 as shown; Forehead support 310 includes a SpO2 sensor 302 (shown in dashed lines) that positions directly above a patient's supraorbital artery when forehead support 310 straps to the patient (e.g., patient 170, FIG. 2). SpO2 sensor cable 312 supplies power to, and transmits oximetry data from, SpO2 sensor 302. Forehead support 310 also includes an air bladder 304 that contacts with SpO2 sensor 302. Bladder 304 may be used to regulate pressure of SpO2 sensor 302 on the forehead of the patient, to reduce errors in SpO2 measurements due to insufficient or excess pressure. Bladder 304 connects through a forehead pressure tube 314 to a PTM module (e.g., PTM module 110(2) of FIG. 5). Tube 308, sensor cable 312 and tube 314 may couple together to form sensor harness 350; harness 350 may, in turn, integrate with air hose 184(2) to form air tube harness 340.

Figure 5:
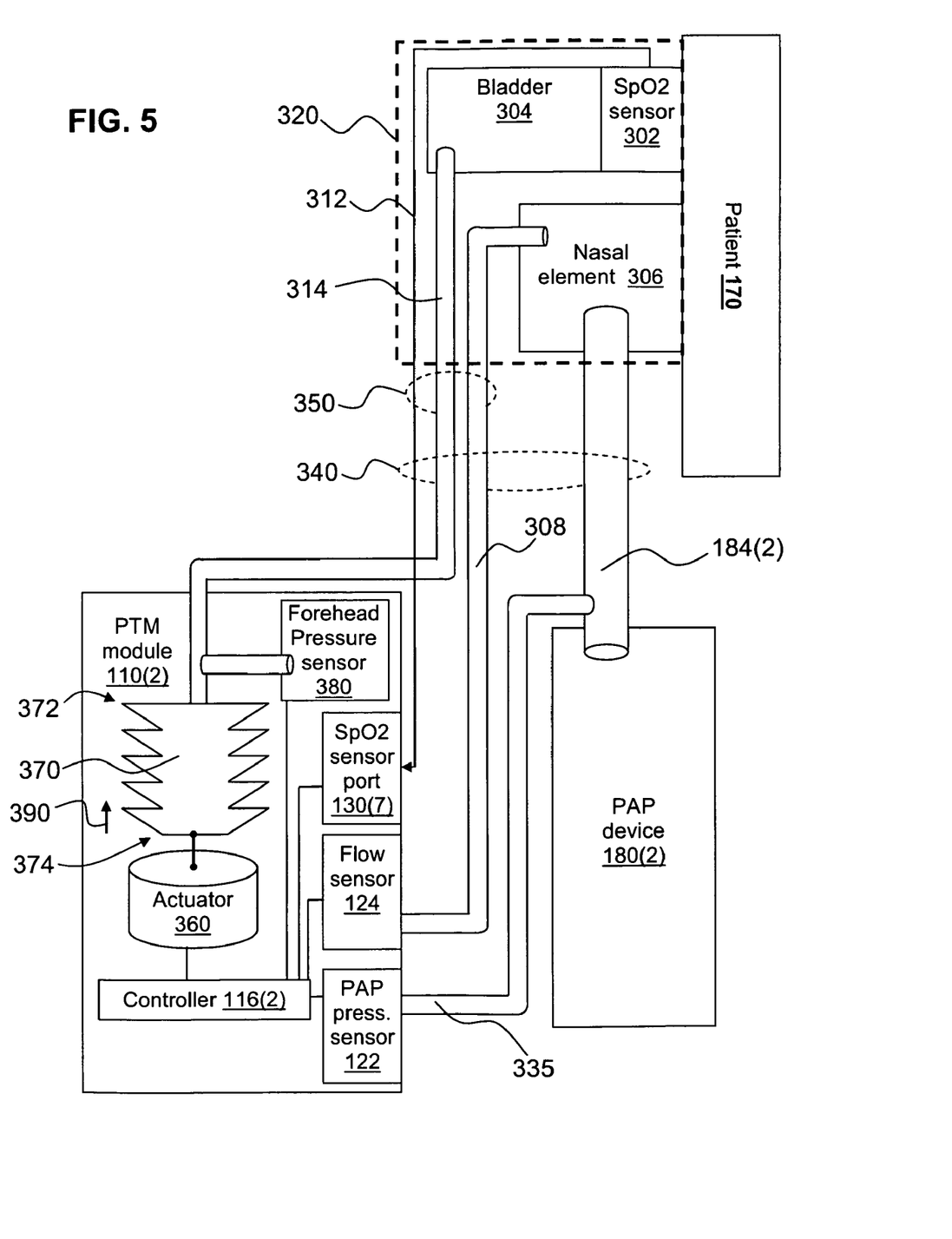
FIG. 5 schematically illustrates certain connections of and between a PAP mask, a PTM module, a PAP device, and a patient.

FIG. 5 illustrates certain connections of and between PAP mask 320, PTM module 110(2), PAP device 180(2) and patient 170, in accord with one embodiment. PAP device 180(2) supplies air to air hose 184(2). PAP mask 320 includes nasal element 306, SpO2 sensor 302 and bladder 304, and connects with air hose 184(2), pressure tube 308, forehead pressure tube 314 and SpO2 sensor cable 312 as shown in FIG. 4. PTM module 110(2) has a controller 116(2), an SpO2 sensor port 130(7), a flow sensor 124 and a PAP pressure sensor 122, similar to like-numbered items of PTM module 110(1), FIG. 1 and FIG. 2 (other elements of PTM module 110(1) may also be present in PTM module 110(2) but are not shown in FIG. 5 for clarity of illustration). Within PTM module 110(2), forehead pressure tube 314 branches to connect with a bellows 370 and a forehead pressure sensor 380 that transmits forehead pressure data to controller 116(2).

Controller 116(2), operating under control of software (e.g., firmware 118, FIG. 2) controls pressure within forehead pressure tube 314, and thus within bladder 304, as follows. Bellows 370, forehead pressure tube 314 and bladder 304 form a closed system with an internal pressure that may be changed by manipulating bellows 370. One end 372 of bellows 370 is mechanically fixed to support structure (not shown) within PTM module 110(2). Another end 374 of bellows 370 attaches to an actuator 360 controlled by controller 116(2). When controller 116(2) receives forehead pressure data indicating pressure within tube 314 that is lower than desired, controller 116(2) operates actuator 360 to push end 374 of bellows 370 in the direction of arrow 390, to compress bellows 370 and raise pressure within the closed system. When controller 116(2) receives forehead pressure data indicating pressure within tube 314 that is higher than desired, controller 116(2) operates actuator 360 to push end 374 of bellows 370 in the opposite direction of arrow 390, to expand bellows 370 and reduce pressure within the closed system.

Thus, bladder 304, forehead pressure tube 314, forehead pressure sensor 380, bellows 370 and actuator 360 form a pneumatic subsystem for regulating pressure of SpO2 sensor 302 on the forehead of a patient. The pressure supplied by the pneumatic subsystem may be regulated by controller 116(2) in a pressure range that maximizes repeatability of SpO2 measurements while avoiding injury to the skin under the sensor; this pressure range may be, for example, 40 mm to 60 mm of mercury.

Changes may be made in the implementation of SpO2 sensor 302 within PAP mask 320 without departing from the scope hereof. For example, SpO2 sensor 302 may mount within PAP mask 320 without pressure regulation as supplied by bladder 304. In another example, pressure regulation may occur differently but with similar outcome. In yet another example, an actuator (e.g., actuator 360) that manipulates bellows 370 may include an electric motor, a piezoelectric transducer and/or mechanical elements such as levers, gears and springs. Alternatively, the pneumatic subsystem may be replaced by a mechanical subsystem that uses mechanical elements and/or actuators within forehead support 310 to regulate the pressure of SpO2 sensor 302 against a patient's forehead.

Figure 6:
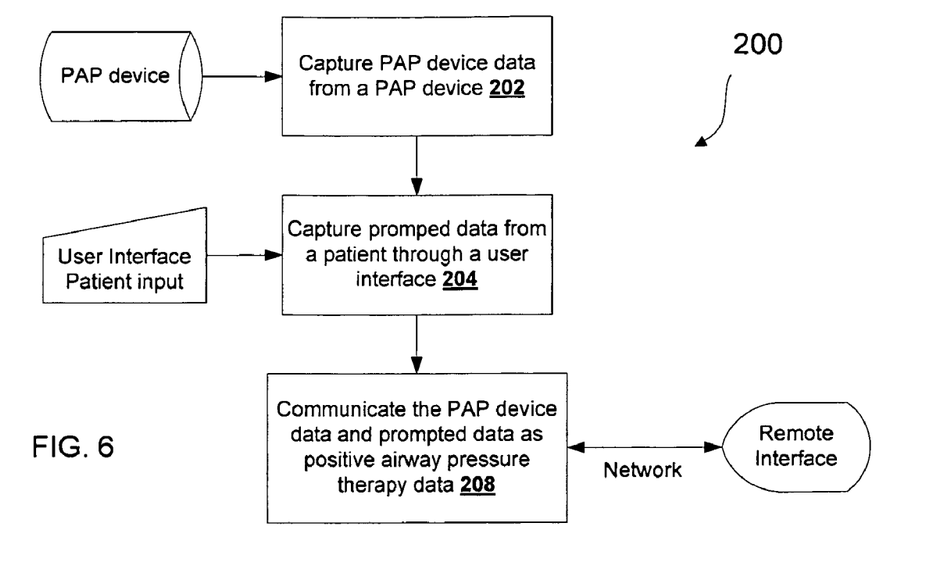
FIG. 6 is a flow chart of one process for managing positive airway pressure therapy.

FIG. 6 is a flow chart of one process 200 for managing positive airway pressure therapy. The steps in FIG. 6 may be performed by a controller (e.g., controller 116(1) or 116(2)) via software (e.g., firmware 118, FIG. 2). Step 202 of process 200 captures PAP device data from a PAP device. In an example of step 202, PTM module 110(1) captures PAP device data from PAP device 180(1). Step 204 of process 200 captures prompted data through a user interface. In an example of step 204, PTM module 110(1) captures prompted data from patient 170 through user interface 114. Step 208 communicates the PAP device data and prompted data as positive airway pressure therapy data over a network. In an example of step 208, controller 116(1) transmits processed first and second data over network 152, to a display viewed by remote professionals at interface 154, FIG. 1. Steps 202-208 need not be undertaken in the order shown by the flowchart of FIG. 6; for example, steps 202 and 204 can be performed in a different order and can be repeated as often as desired.

Figure 7:
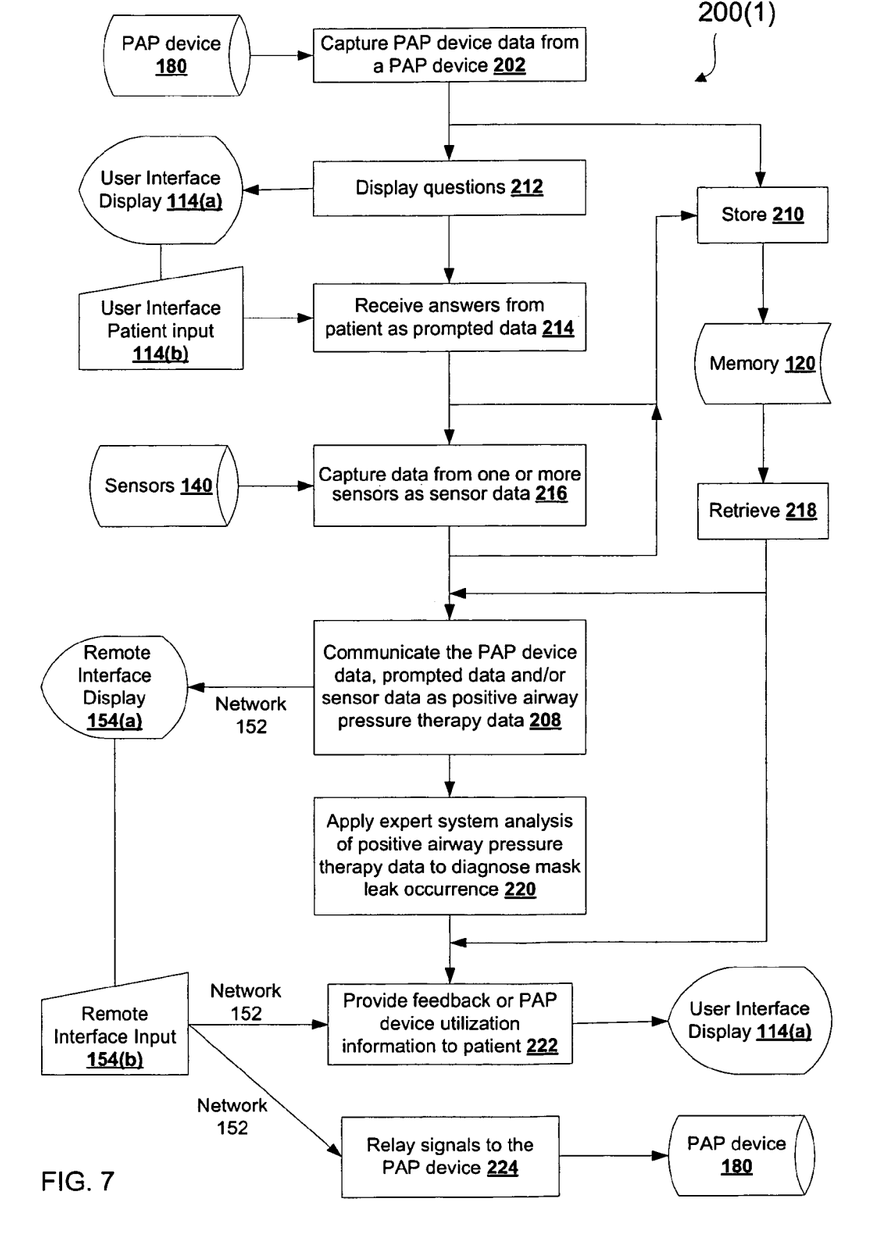
FIG. 7 is a flow chart of one process for managing positive airway pressure therapy.

FIG. 7 is a flow chart of one process 200(1) for managing positive airway pressure therapy. The steps of FIG. 7 may be performed by a controller (e.g., controller 116(1) or 116(2)) via software (e.g., firmware 118, FIG. 2). In step 202, process 200(1) captures data from a PAP device. In an example of step 202, controller 116 captures PAP device data from PAP device 180(1) or 180(2)). Step 210 stores the PAP device data in memory for later use. In an example of step 210, controller 116 stores the PAP device data in memory 120, FIG. 2. Step 212 displays one or more questions to a patient. In an example of step 212, controller 116(1) displays the questions on display 114A of PTM device 110(1)); this in turn may prompt a reply by patient 170, e.g., through input user interface 114(b). Step 214 receives this reply as prompted data, and step 210 stores the prompted data, for example, in memory 120. Step 216 captures sensor data from one or more sensors attached to a patient. In an example of step 216, controller 116 captures sensor data from sensors 140 attached to patient 170. In step 210, process 200(1) stores this data in memory (e.g., memory 120). Step 218 retrieves data (e.g., any of PAP device data, prompted data or sensor data) from the memory for communication over a network (e.g., network 152) or for use in a calculation.

In step 208, process 200(1) communicates the prompted data (and, optionally, PAP device data and/or sensor data) as positive airway pressure therapy data over the network to a display (e.g., display 154(a)) that may be viewed by remote professionals. Step 220 applies expert system analysis to the positive airway pressure therapy data, to diagnose the occurrence of mask leak events.

Step 218 retrieves stored PAP device utilization information from the memory. Step 222 provides feedback or PAP device utilization information to the patient through a user interface (e.g., user interface 114, FIG. 2). PTM module 110 may initiate step 222 as a result of detecting a mask leak event, for example; or remote professionals may initiate step 222 by sending a command to PTM module 110 through network 152. Step 224 relays commands to the PAP device. In an example of step 224, PTM module 110 receives commands issued through network 152 by remote professionals, and transmits these commands to PAP device 180(1)).

The steps of process 200(1) shown in FIG. 7 need not be undertaken in the order shown, and may repeat as needed or desired.

In one example of operation, patient 170 may turn on a PTM module 110 (e.g., PTM module 110(1)) when he or she is ready to go to bed; the PTM module then (1) displays a question on user interface 114 related to the patient's previous night's use of PAP device 180(1) and PTM module 110(1), (2) receives answers to these questions through user interface 114 (step 214), (3) stores these answers as data (step 210), (4) displays further questions and receives further answers (repeating steps 212 and 214), (5) retrieves stored information about PAP device utilization (step 218), (6) provides feedback or PAP device utilization information to the patient (step 222), and (7) collects and stores data (repeating steps 202, 216, and 210) as patient 170 begins use of PAP device 180(1) for the night.

Other steps may be added to process 200(1) described in FIG. 7. Further, PTM module 110 may perform process steps continuously or upon request. For example, PTM module 110 may be configured to continuously analyze data received from a patient, to identify the occurrence of apnea or hypopnea events. A PTM module 110 which identifies apnea or hypopnea events may also be configured to initiate adjustments to the therapeutic conditions applied by a PAP device 180. Adjustments to therapeutic conditions may be directly communicated from PTM communication port 160 to a communication port 182 of PAP device 180; or, instructions for making such adjustments may be provided to a patient through user interface 114 (when PAP device 180 does not have a communication port 182).

Changes may be made in and to process 200 and/or process 200(1) without departing from the scope hereof. For example; if a PAP device 180 is not configured for communication with a PTM module 110, step 202 may be omitted. If sensors 140 are not used; step 216 of process 200(1) may be omitted.

Changes may be made in the above methods and systems without departing from the scope hereof. It should thus be noted that that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A positive airway pressure therapy management module, comprising:
   a data port for capturing data from a PAP device that is separate from the management module;

one or more sensor ports configured with the management module and also separate from a PAP device, for direct interface with one or more sensors that generate sensor data;

a user interface for capturing prompted data;

a controller for processing one or more of the prompted data, the sensor data and the PAP device data and for communicating one or more of the prompted data, the sensor data and the PAP device data as positive airway pressure therapy data over a network; and memory for storing the prompted data, the sensor data and the PAP device data.

2. The module of claim 1, wherein the user interface is configured to display information and questions, and to receive answers, as prompted data.

3. The module of claim 1, wherein the controller stores the positive airway pressure therapy data while offline from the network, and wherein, when the controller is online with the network, the controller responds to a request over the network to communicate stored positive airway pressure therapy data over the network.

4. The module of claim 1, wherein the controller communicates the positive airway pressure therapy data over the network to a remote interface, in real time.

5. The module of claim 1, the controller comprising firmware that is upgradeable over the network.

6. The module of claim 1, further comprising a therapy mask having:

a forehead support for securing the mask to a patient's face, and;

an oximeter sensor configured with the forehead support, for contacting the patient's forehead to provide real-time oxygen saturation data of the patient when the mask is worn during positive airway pressure therapy, wherein the controller processes the prompted data and the oxygen saturation data and communicates the prompted data and the oxygen saturation data as the positive airway pressure therapy data.

7. The module of claim 6, the oximeter sensor configured with the forehead support such that the oximeter sensor rests proximate the patient's supraorbital artery when the mask is worn by the patient; the module further comprising a pneumatic subsystem for regulating pressure of the SpO2 sensor against the forehead of the patient.

8. The module of claim 7, the sensor selected from the group of a flow sensor, a forehead pressure sensor and an air pressure sensor.

9. The module of claim 1, wherein at least one of the one or more additional sensor ports comprises one of a pressure sensor port, a flow sensor port, an EKG sensor port, an $SpO_2$ sensor port, a respiration effort sensor port and a snore sensor port.

10. The module of claim 1, the controller configured to calculate one or more of an Apnea Hypopnea Index, a Respiratory Disturbance Index and a patient compliance metric as positive airway pressure therapy data.

11. The module of claim 1, the controller configured to perform a pressure titration using the PAP device.

12. The module of claim 11, the controller responsive to commands from the network to initiate performance of the pressure titration.

13. The module of claim 1, the controller configured to analyze the positive airway pressure therapy data to identify one or both of mask leaks and partial upper airway obstruction, and to display an indication of mask leak occurrence through the user interface.

14. The module of claim 1, the controller being responsive to signals over the network to relay commands to the PAP device.

15. A system for managing positive airway pressure therapy of a patient, comprising:

a PAP device; and a management module separate from and communicatively connected with (1) the PAP device, for capturing and storing PAP device data from the PAP device, and (2) one or more sensors that are also separate from the PAP device, for directly capturing data of the patient from the sensors as positive airway pressure therapy data;

the management module configured for communicating the positive airway pressure therapy data to a remote interface, separate from the PAP device, over a network.

16. A software product comprising instructions, stored on computer-readable media, wherein the instructions, when executed by a computer, perform steps for managing positive airway pressure therapy of a patient, comprising:

instructions for capturing PAP device data from a PAP device;

instructions for operating a user interface to present information and to capture subjective quality of life responses as prompted data;

instructions for capturing sensor data directly from one or more sensors not associated with the PAP device;

instructions for storing data in memory and retrieving data from memory; and instructions for communicating PAP device data, prompted data and sensor data over a network.

17. The software product of claim 16, further comprising instructions for calculating one or more of an Apnea Hypopnea Index, a Respiratory Disturbance Index, and a pressure titration.

18. A method for managing positive airway pressure therapy of a patient, comprising:

providing a therapy management module, the module having (1) a data port for connection with a separate PAP device, and (2) at least one sensor port configured with the management module and also separate from the PAP device, for connecting with one or more patient-worn sensors;

capturing sensor data directly from the one or more patient-worn sensors via the at least one sensor port;

communicating the sensor data as positive airway pressure data over a network, to a remote location;

accepting a treatment command from the remote location over the network, at the management module; and modifying therapeutic conditions supplied by the PAP device, according to the treatment command, when the management module connects with the PAP device via the data port.

19. The method of claim 18, further comprising capturing data from a PAP device as PAP device data; and communicating the PAP device data and the sensor data to the remote location as the positive airway pressure data.

20. The method of claim 19, further comprising storing at least one of the PAP device data and the sensor data as stored positive airway pressure therapy data, and wherein communicating comprises communicating the stored positive airway pressure therapy data over the network when the management module is online with the network.

21. The method of claim 18, wherein the step of communicating the positive airway pressure therapy data over the network occurs in response to a query from the network to the management module.

22. The method of claim 18, wherein capturing the sensor data from the one or more sensors connected to the patient comprises one or more of:
   capturing airway pressure sensor data;
   capturing flow sensor data;
   capturing EKG sensor data;
   capturing SpO$_2$ sensor data;
   capturing respiration effort sensor data; and
   capturing snore sensor data.

23. The method of claim 18, further comprising calculating, in response to a calculation command from the remote location, one or more of an Apnea Hypopnea Index, a Respiratory Disturbance Index and a patient compliance metric.

24. The method of claim 18, wherein modifying therapeutic conditions comprises performing a pressure titration in response to the treatment command.

25. The method of claim 18, wherein modifying therapeutic conditions comprises relaying commands from the management module to the PAP device in response to the treatment command from the remote location.

26. The method of claim 18, further comprising prompting for data via a user interface and capturing data entered via the user interface as prompted data.

27. The method of claim 26, wherein capturing prompted data through the user interface comprises displaying questions and receiving answers.

28. The method of claim 26, further comprising displaying information through the user interface, the information comprising at least one of information relating to the therapeutic conditions supplied by the PAP device, instructions for utilizing the PAP device and suggestions for utilizing the PAP device.

29. The method of claim 26, wherein communicating comprises communicating the sensor data and the prompted data over the network as the positive airway pressure data.

30. The method of claim 29, further comprising:
   storing at least one of the prompted data and the sensor data as stored positive airway pressure data,
   wherein communicating comprises communicating the stored positive airway pressure therapy data over the network when the management module is online with the network.

31. A positive airway pressure therapy management module comprising:
   a data port for capturing data from a PAP device that is separate from the management module;
   at least one sensor in the module and also separate from a PAP device, for sensing a condition of a patient and generating sensor data;
   tubing for facilitating pneumatic communication between the sensor and the patient;
   a controller for processing one or both of the PAP device data and the sensor data, and for communicating one or more of the sensor data and PAP device data as positive airway pressure therapy data over a network; and
   memory for storing the sensor data and the PAP device data.

* * * * *